United States Patent [19]

Schumacher et al.

[11] Patent Number: 4,863,931
[45] Date of Patent: Sep. 5, 1989

[54] ANTIHISTAMINIC FLUORO SUBSTITUTED BENZOCYCLOHEPTAPYRIDINES

[75] Inventors: Doris P. Schumacher, Florham Park; Bruce L. Murphy, Glen Ridge; Jon E. Clark, Highland Park, all of N.J.

[73] Assignee: Schering Corporation, Kenilworth, N.J.

[21] Appl. No.: 244,768

[22] Filed: Sep. 15, 1988

[51] Int. Cl.$^4$ .................. A61K 31/445; C07D 401/04
[52] U.S. Cl. ...................................... 514/290; 546/93
[58] Field of Search ........................... 546/93; 514/290

[56] References Cited

U.S. PATENT DOCUMENTS 3,326,924 6/1967 Villani .................................. 546/93
3,717,647 2/1973 Villani .................................. 546/315
4,282,233 8/1981 Villani ................................... 514/290
4,731,447 3/1988 Schumacher et al. ................ 546/93

FOREIGN PATENT DOCUMENTS 0042544 10/1984 European Pat. Off. .

OTHER PUBLICATIONS

F. Villani et al., *J. Med. Chem.*, vol. 15, No. 7, pp. 750-754 (1972).
F. Villani et al., *Arzneim-Forsch.*, vol. 36, pp. 1311-1314 (1986).

Primary Examiner—Richard A. Schwartz
Attorney, Agent, or Firm—Henry P. Nowak; James R. Nelson

[57] ABSTRACT

Certain benzocycloheptapyridine compounds with fluorine substitution across the exocyclic double bond are prepared and they are useful as antihistaminic agents.

14 Claims, No Drawings

ANTIHISTAMINIC FLUORO SUBSTITUTED BENZOCYCLOHEPTAPYRIDINES

BACKGROUND OF THE INVENTION

The present invention relates to certain benzocycloheptapyridines having fluoro substitution across an exocyclic double bond.

Numerous benzocycloheptapyridine compounds having substitution on the tricyclic ring system and having hydrogenated exocyclic double bonds have been disclosed. See, for example, U.S. Pat. Nos. 3,326,924, 3,717,647 and 4,282,233, European published Application No. 0042544, Villani et al., *Journal of Medicinal Chemistry*, Vol. 15, No. 7, pp 750–754 (1972) and *Arzneim. Forsch.*, 36, pp 1311–1314 (1986). However, fluoro-substitution across the exocyclic double bond has not previously been disclosed or suggested.

U.S. Pat. No. 4,731,447 in column 8, lines 31–35 discloses that in the preparation of certain benzocycloheptapyridine compounds using HF/BF$_3$ the temperature may be controlled so as to minimize side reactions, such as HF addition to the double bond of the rings.

SUMMARY OF THE INVENTION

It has now surprisingly been found that antihistamine activity is possessed by compounds represented by structural formula I

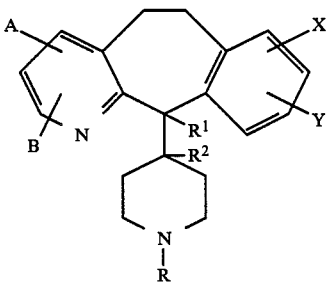

or a pharmacuetically acceptable salt thereof, wherein:

A, B, X and Y may be the same or different, and each independently represents H, halo, —CF$_3$, —C(O)R$^{10}$, —SR$^{10}$, —N(R$^{10}$)$_2$, —NO$_2$, —OC(O)R$^{10}$, —CO$_2$R$^{10}$, —OCO$_2$R$^{11}$, alkyl, alkenyl or alkynyl, which alkyl or alkenyl groups may be substituted with halo, —OR$^{10}$, or —CO$_2$R$^{10}$;

each R$^{10}$ independently represents H, alkyl or aryl;

R$^{11}$ represents alkyl or aryl;

R$^1$ and R$^2$ represent H and F respectively or F and H respectively; and

R represents H, alkyl or —C$_2$R$^{10}$ wherein R$^{10}$ is as previously defined.

The invention also relates to a pharmaceutical composition comprising a compound of formula I in combination with a pharmaceutically acceptable carrier and to a method of treating allergic reactions by administering to a mammal in need of such treatment an antihistaminic effective amount of a compound of formula I.

In a preferred embodiment of the invention, one of A, B, X and Y is halo, e.g., chloro or fluoro, and the other groups are H.

In another preferred embodiment of the invention, R is —CO$_2$R$^{10}$, where R$^{10}$ is H or alkyl, and most preferably alkyl, e.g., ethyl. In yet another preferred embodiment of the invention, R$^1$ is fluoro, and R$^2$ is H.

Preferred species falling within the scope of formula I include: ethyl 4-[8-chloro-6,11-dihydro-5H-benzo[5,6]cyclohepta[1,2-b]pyridin-11-yl]-4-fluoro-1-piperidinecarboxylate; and ethyl 4-[8-chloro-11-fluoro-6,11-dihydro-5H-benzo[5,6]cyclohepta[1,2-b]pyridin-11-yl]-1-piperidine-carboxylate.

DETAILED DESCRIPTION OF THE INVENTION

Certain compounds of formula I may exist in different isomeric as well as conformational forms. The invention contemplates all such isomers both in pure form and in admixture, including racemic mixtures.

The compounds of formula I can exist in unsolvated as well as solvated forms, including hydrated forms, e.g., hemihydrate. In general, the solvated forms, with pharmaceutically acceptable solvents such as water, ethanol and the like, are equivalent to the unsolvated forms for purposes of the invention.

Certain compounds of formula I will be acidic in nature, e.g. those compounds which possess a carboxylic or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of formula II also form pharmaceutically acceptable salts, e.g., acid addition salts and quaternary ammonium salts. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to product a salt in the conventional manner. The free base forms may be regenerated by treating the salt with a suitable dilute aqueous base solution such as dilute aqueous sodium hydroxide, potassium carbonate, ammonia and sodium bicarbonate The quaternary ammonium salts are prepared by conventional methods, e.g., by reaction of a tertiary amino group in a compound of formula II with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

When utilized herein, the terms below, unless otherwise indicated, have the following scope:

halo—represents fluoro, chloro, bromo and iodo;

alkyl (including the alkyl portions of alkoxy, alkylamino and dialkylamino)—represents straight or branched carbon chains, which contain from 1 to 6 carbon atoms;

alkenyl—represents straight or branched carbon chains having at least one carbon to carbon double bond and preferably having from 2 to 6 carbon atoms;

alkynyl—represents straight or branched carbon chains having at least one carbon to carbon triple bond and preferably having from 2 to 6 carbon atoms;

aryl—represents a carbocyclic group containing from 6 to 15 carbon atoms and having at least one aromatic ring (e.g., a phenyl or fused benzene ring), with all available substitutable carbon atoms of the carbocyclic group being intended as possible points of attachment, said carbocyclic group being optionally substituted with 1 to 3 groups, each independently selected from halo, alkyl, hydroxy, alkoxy, phenoxy, amino, alkylamino, dialkylamino. Preferred aryl groups include phenyl and 4-chlorophenyl.

The lines drawn from the groups A, B, X and Y into the pyridine and benzene rings of formula I are intended to indicate that such groups may be substituted on any carbon of such rings.

Compounds A and B above were prepared as side-products of the reactions described in U.S. Pat. No. 4,731,447. The methods described in that patent may be employed to prepare the compounds of the invention as described further below.

Compounds of general formula I may be prepared as shown in Scheme 1 below wherein A, B, X, Y, $R^1$, $R^2$, $R^{10}$ and $R^{11}$ are as defined above and $R^6$ and $R^a$ are as defined below. The general method for producing compounds of general formula I from compounds of general formula 3 is outlined by reactions (a) through (g) in Scheme 1. Compounds of general formula 3 may be readily prepared as described in March, J. *Advanced Organic Chemistry*, 3rd Edition, John Wiley & Sons (1985), pp. 496–97; Villani et al, *J. Heterocyclic Chem.*, 8, 73 (1971) or may be obtained from commercial sources, e.g. Reilly Tar and Chemical.

SCHEME 1

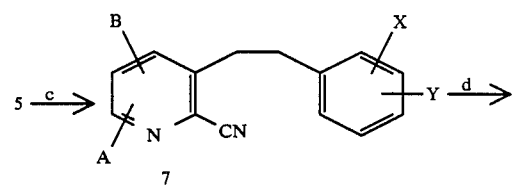

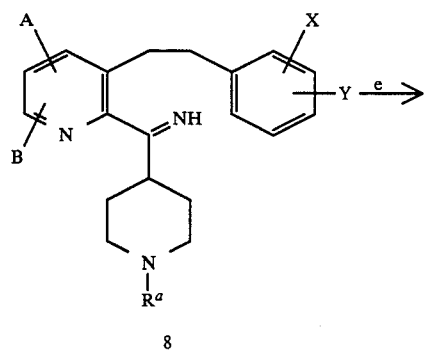

-continued
SCHEME 1

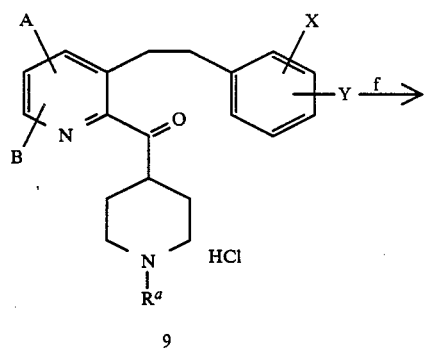

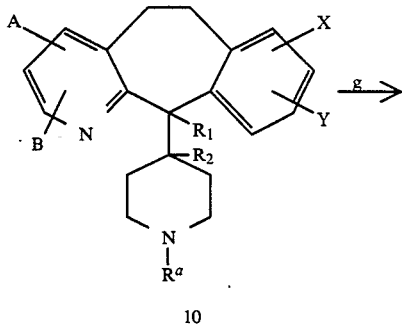

Reaction (a): A compound of formula 3, e.g., an unsubstituted or substituted 2-cyano-3-methyl-pyridine, can be converted into the corresponding carboxylic acid, e.g., an appropriate 3-methyl-2-pyridine carboxylic acid or activated ester thereof, e.g., a succinimide or hydroxysuccinimide ester, by reactions conventional in the art e.g., hydrolysis or esterification. The carboxylic acid or activated ester thereof can then be reacted with the appropriate amino compound of formula $NH_2R^6$ to form a compound of formula 4

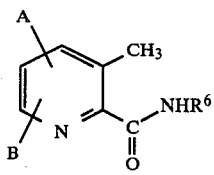

(4)

wherein $R^6$ is a protecting group that will protect the N of the group $CONHR^6$ in formula 4 from reaction with an alkylating agent. Preferably the protecting group is a tertiary butyl group.

A compound having such an $R^6$ tertiary butyl group can also be obtained directly from a compound of formula 3, for example, by a Ritter reaction in which a tertiary butyl compound is reacted with a 2-cyano-3-methyl-pyridine compound to produce a compound of formula 4a.

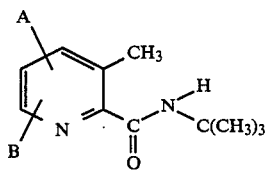

(4a)

This reaction is generally performed in an acid such as concentrated sulfuric acid or concentrated sulfuric acid in glacial acetic acid. Suitable tertiary butyl compounds include, but are not limited to, t-butyl iodide, t-butyl chloride, t-butyl bromide, t-butyl iodide, isobutylene or any other compound which under hydrolytic conditions forms t-butyl carboxamides with cyano compounds. The temperature of the reaction will vary depending on the reactants, but generally is conducted in the range of from about 50° to about 100° C. with t-butyl alcohol. The reaction may be performed with inert solvents but is usually run neat.

Reaction (b): The compound of formula 4 may be reacted with an appropriate benzyl halide of the formula

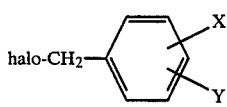

in the presence of a base to form the compound of formula 5 above. The halide is preferably Cl, Br or I, more preferably Cl. Examples of appropriate benzyl halides include, but are not limited to, benzyl chloride, 3-chlorobenzyl chloride, 3-fluorobenzyl chloride, 3,4-dichlorobenzylchloride, 4-fluorobenzyl chloride, 3-nitrobenzyl chloride, 3-methylbenzyl chloride, etc. Any suitable base can be employed, e.g., an alkyl lithium compound such as n-butyl lithium in tetrahydrofuran (THF). Preferably the base has a $pK_a$ of greater than 20 and more preferably greater than 30. This reaction can be conducted at any suitable temperature, e.g., temperatures of from about $-78°$ C. to about 30° C., preferably from about $-40°$ C. to about $-30°$ C. The reaction can be performed in any suitable inert solvent such as THF, diethyl ether, etc.

Reaction (c): The amide of formula 5 may be converted to the cyano compound of formula 6 by the use of a suitable dehydrating agent such as $POCl_3$, $SOCl_2$, $P_2O_5$, toluene sulfonyl chloride in pyridine, oxalyl chloride in pyridine, etc. This reaction can be performed in the absence of or with an inert co-solvent such as xylene. The dehydrating agent such as $POCl_3$ is employed in equivalent amounts or greater and preferably in amounts of from about 2 to about 15 equivalents. Any suitable temperature and time can be employed for performing the reaction, but generally heat is added to speed up the reaction. Preferably, the reaction is performed at or near reflux.

Reaction (d): The cyano compound of formula 6 may be reacted with a Grignard reagent prepared from the appropriate 1-(N-protected)-4-halopiperidine. Any suitable N-protecting group known in the art to protect the piperidinyl nitrogen atom from reaction during formation of the Grignard reagent can be employed. Suitable N-protecting groups include alkyl (e.g. methyl), aryl (e.g. phenyl or substituted phenyl), alkyloxyalkyl (e.g. methoxymethyl), benzyloxyalkyl (e.g. benzyloxymethyl), substituted benzyloxyalkyl (e.g. (di-p-methoxyphenyl) methyl), triphenylmethyl, tetrahydropyranyl, diphenyl phosphinyl, benzene sulfenyl, etc. The N-protecting group can be later removed by conventional means once the Grignard reagent has been reacted with the compound of formula 6.

The reaction between compounds of formula 6 and the Grignard reagent are generally performed in an inert solvent such as an ether, toluene or tetrahydrofuran. This reaction is performed under the general conditions for a Grignard reactions, e.g., at temperatures of from about 0° C. to about 75° C.

Reaction (e): The resulting intermediate of formula 8, wherein $R^a$ is an alkyl group, may be hydrolyzed, e.g., with aqueous acid such as aqueous HCl, to prepare the corresponding ketone of formula 9.

Reaction (f): The compound of formula 9 can be ring-closed to form the desired cycloheptene ring system (formula 10) by treating the compound 9 with a super acid having a Hammett acidity function of less than about minus 12, e.g., minus 13, minus 14, etc. This measure of acidity is defined in Hammett, Louis P., and Deyrup, Alden J., "Journal of the American Chemical Society", Vol. 54, 1932, p. 2721. Suitable super acids for this purpose include, for example, $HF/BF_3$. The reaction can be performed in the absence of or with a suitable inert co-solvent such as $CH_2Cl_2$. The temperature and time of the reaction vary with the acid employed.

The temperature may be controlled so as to maximize the side reaction of HF addition to the exocyclic double bond. Consequently, the temperature is generally in the range of from about $+5°$ to $-50°$ C., preferably from about 0° to $+5°$ C.

Generally, the super acid is employed in excess, preferably in amount of from about 1.5 to about 30 equivalents. For example, with $HF/BF_3$ as the super acid system the volume/weight ratio of HF to the compound of formula IX in the reaction mixture is preferably from about 30 to about 1.5, more preferably 2.5 to 1.5. In such system, the weight/weight ratio of $BF_3$ to the compound of formula 9 in the reaction mixture is preferably from about 15 to about 0.75, more preferably from about 1 to about 0.75.

Reaction (g): The alkyl group ($R^a$) on the piperidyl ring (when it is methyl) may be converted to the alkyl esters of the formula Ia by reacting a compound of general formula 10 with an alkyl chloroformate, preferably ethyl chloroformate as described in Villani et al., Arzneim.—Forsch/Drug Research 1986, 36, 1311–1314 and in U.S. Pat. No. 4,731,447.

In the above processes a-g, it is sometimes desirable and/or necessary to protect certain A, B, X, Y, etc., groups during the reactions. Conventional protecting groups are operable. For example, the groups listed in column 1 of the following table may be protected as indicated in column 2 of the table:

| 1. Group to be protected | 2. Protected Group |
| --- | --- |
| —COOH | —COOalkyl, —COObenzyl, —COOphenyl |
| >NH | >N—CO₂alkyl, >N—CO₂benzyl, >N—CO₂CH₂CCl₃ |
| >CO | (cyclic ketal structures) |
| —OH | —O-(tetrahydropyranyl), —O—CH₃ |
| —NH₂ | —N(succinimido) |

Of course, other protecting groups well known in the art may be used. After the reaction or reactions, the protecting groups may be removed by standard procedures.

Conversion of compounds of formula Ia to compounds of formula I wherein R is H can be accomplished by hydrolysis the —CO₂R¹⁰ group. Hydrolysis may occur in an organic or inorganic polar solvent by refluxing in the presence of a base or acid. A typical hydrolyzing reaction utilizes 30% HCl solution in ethanol.

The compounds of the present invention can be used as antihistamines. One method of measuring the antihistamine activity of the compounds of the present invention in vitro utilizes isolated preparation of guinea pig ileum as described below and in Tozzi et al., Agents and Actions, 4(4):264 (1974).

Guinea Pig Ileum

Antagonists were evaluated for their ability to inhibit the spasmogenic doses of histamine dihydrochloride ($1.8 \times 10^6$M) and acetylcholine chloride ($1.3 \times 10^{-7}$M) on separate ileal segments of guinea-pig intestine according to the classical isotonic technique described in Magnus, Pflugers Arch. Ges. Physiol., 102:123 (1904). Freshly cut 2 cm segments of ileum were removed from male albino guinea-pigs (300–500 g) and suspended in 10 ml perfusion baths containing Tyrode solution warmed to 32° C. and constantly aerated with 95% $O_2$ and 5% $CO_2$. Tissues were adjusted to 0.5-1 g tension and allowed to equilibrate for a period of 30 minutes. All responses were recorded by means of a Harvard smooth muscle transducer connected to a Harvard electronic recorder. Utilizing 3-4 logarithmically-spaced doses of the antagonist, a graded inhibition of the smooth muscle response to histamine or acetylcholine was obtained by alternating the dose of agonist with increasing doses of antagonist. The agonists, in volumes of 0.1 ml, were added to the bath and kept in contact with the tissues for 45 seconds before they were removed by washing. In general, 3 control contractions of approximately equal height were obtained prior to studying the antagonist. The antagonist, in volumes between 0.1 and 0.3 ml, was added to the bath and allowed to remain for 3 minutes before the agonist was added. Then both were removed by washing and the next log increment of the antagonist was used.

At least 5 separate dose-response patterns were attained in each drug assay utilizing 2-5 segments. The average percent inhibition of agonist in all trials was then calculated. The results for the compound 8-chloro-6,11-dihydro-11-fluoro-11-(1-methyl-4-piperidinyl)-5H-benzo[5,6]cyclohepta[1,2-b]pyridine are shown in Table 1.

TABLE 1

| Molar Conc. of Histamine | % of Maximum Response for Histamine | % of Maximum Response for Histamine in the Presence of Test Compound |
| --- | --- | --- |
| $10^{-8}$ | 11 ± 3 | 2 ± 0.9 |
| $3 \times 10^{-8}$ | 17 ± 4 | 5 ± 1 |
| $10^{-7}$ | 35 ± 7 | 8 ± 1 |
| $3 \times 10^{-7}$ | 56 ± 4 | 18 ± 4 |
| $10^{-6}$ | 81 ± 7 | 32 ± 3 |
| $3 \times 10^{-6}$ | 96 ± 3 | 42 ± 3 |

The following test procedure may be used to demonstrate antihistaminic activity of compounds of formula I. Protection against histamine lethality in the following assay is indicative of strong antihistaminic properties.

Prevention of Histamine-Induced Lethality in Guinea Pigs

Compounds may be evaluated for antihistamine activity by their ability to protect female albino guinea pigs (250–350 g) against death induced by the intravenous injection of histamine dihydrochloride at 1.1 mg/kg, which is approximately twice the $LD_{99}$. Doses of the antagonists were administered orally to separate groups of fasted animals 1 hour prior to the challenge with histamine and protection from death recorded for 30 minutes after histamine.

At a dose of 1 mg/kg p.o. of ethyl 4-[8-chloro-11-fluoro-6,11-dihydro-5H-benzo[5,6]cyclohepta [1,2-b]pyridin-11-yl]-1-piperidinecarboxylate, 4 of 5 animals survived the dose of histamine dihydrochloride.

The compounds of formula I can be administered in any number of conventional dosage forms. Solid dosage forms include capsules, tablets, pills, powders, suspensions, solutions, cachets or suppositories. Parenteral preparations include sterile solutions or suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, color agents, stabilizing agents, emulsifying agents, dispersing agents, suspending agents, perfumes, preservatives, lubricants, etc.

When used orally or parenterally as antihistamines, the compounds of the invention can be administered in an amount ranging from about 0.1 mg/kg to about 100 mg/kg, preferably from 0.01 mg/kg to about 25 mg/kg per day. Determination of the proper dosage of a compound of the invention for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition and size of the patient as well as severity of the disease being treated.

The following examples illustrate specific embodiments of the present invention including preparation of compounds, intermediates and starting materials.

EXAMPLE 1

A.
N-(1,1-dimethylethyl)-3-methyl-2-pyridinecarboxamide

A suspension of 2-cyano-3-methyl pyridine (400 g; 3.4 mol) in 800 mL of t-butanol was heated at 70° C. Concentrated sulfuric acid (400 mL) was added over 45 min. The reaction was complete after a further 30 min. at 75° C. The reaction mixture was diluted with water (400 mL) and toluene (600 mL) and brought to pH 10 with concentrated aqueous ammonia. The temperature was kept at 50°–55° C. during work-up. The toluene phase was separated, the aqueous layer extracted again with toluene and the combined toluene phases were washed with water. Removal of the toluene yielded 633 g (97%) of crystalline N-(1,1-dimethylethyl)-3-methyl-2-pyridinecarboxamide: m.p. 56°–58° C.; NMR 9200 MHz, CDCl$_3$)δ1.52 (s,9H); 2.75 (s,3H); 7.25 (dd,1H, J=7.5, 5 Hz); 7.58 (dd,1H, J=7.5, 1.2 Hz); 8.08 (br s, 1H); 8.40 (dd,1H, J=5), 1.2 Hz); mass spectrum, m/e (rel intensity) 192M+ (12), 177 (49). Anal. Calcd for C$_{11}$H$_{16}$N$_2$O: C,68.68; H, 8.13; N,14.40. Found: C,68.71; H,8.39; N,14.57.

B.
3-[2-(3-Chlorophenyl)ethyl]-N-(1,1-dimethylethyl)-2-pyridine carboxamide To a cold (−40° C.) solution of N-(1,1-dimethylethyl)-3-methyl-2-pyridinecarboxamide (31.5 g; 0.16 mol) in 600 mL of dry tetrahydrofuran was added n-butyllithium in hexanes (2.5 mol; 131 mL) while the temperature was maintained at −40° C. The solution turned deep red after one equivalent was added. Sodium bromide (1.6 g) was added and the mixture was stirred for 10 min. A solution of m-chlorobenzyl-chloride (26.5 g; 0.174 mol) in 125 mL of dry tetrahydrofuran (THF) was added while the temperature was again maintained at −40° C. The reaction mixture was stirred for a further 30 min. after which water was carefully added until the color dissipated. The product was isolated by extraction into ethyl acetate which was washed with water, dried (MgSO$_4$) and concentrated to give 53.6 g (HPLC purity 89%; yield 92%) of 3-[2-(3-chlorophenyl)ethyl]-N-(1,1-dimethylethyl)-2-pyridine carboxamide as an oil. This oil may be used directly in the next step or crystallized from hexanes to give 3-[2-(3-chlorophenyl)ethyl]-N-(1,1-dimethylethyl)-2-pyridine carboxamide as a white solid: m.p. 45°–46° C.; NMR (200 MHz,CDCl$_3$)δ1.50 (s,9H), 2.96 (t,2H,J=8 Hz); 3.40 (t,2H,J=8 Hz); 7.0–7.3 (m,5H); 7.39 (dd,1H,J=8, 2 Hz); 7.98 (br s, 1H); 8.30 (dd,1H, J=4, 1 Hz); mass spectrum, m/e (rel intensity) 316M+ (19). Anal. Calcd for C$_{18}$H$_{21}$N$_2$OCl: C,68.22; H,6.68; N,8.88; Cl,11.19. Found: C,68.25; H,6.59; N,8.78; Cl,11.10.

C. 3-[2-(3-Chlorophenyl)ethyl]-2-pyridinecarbonitrile

A solution of 3-[2-(3-chlorophenyl)ethyl]-N-(1,1-dimethylethyl)-2-pyridine carboxamide (175 g; 0.55 mol) in 525 mL (5.6 mol) of phosphorous oxychloride was heated at reflux for 3 h. Excess phosphorus oxychloride (−300 mL) was removed by distillation and the remaining solution was carefully poured into ice-water. The pH of the solution was adjusted to 8 with 50% aqueous sodium hydroxide while the temperature was maintained at 25°–30° C. The mixture was stirred for 2h during which time the pH was maintained at 8. The product was collected by filtration, washed with water and dried in a vacuum oven at 50° C. to give 127 g (95%) of crystalline 3-[2-(3chlorophenyl)ethyl]-2-pyridinecarbonitrile: m.p. 72°–73° C.; NMR (200 MHz, CDCl$_3$)δ2.9–3.1 (m,2H), 3.1–3.2 (m,2H), 7.0–7.1 (m,1H), 7.1–7.3 (m,3H), 7.42 (dd,1H,J=7.3, 5 Hz); 7.56 (dd,1H,J=7.3, 1.2 Hz), 8.48 (dd,J=5, 1.2 Hz); mass spectrum, m/e (rel intensity) 242 M+ (18). Anal. Calcd for C$_{14}$H$_{11}$N$_2$Cl: C,69.28; H,4.59; N,11.54; Cl 14.61. Found: C,69.37; H,4.48; N,ll.39; Cl,14.48.

D.
[3-[2-(3-chlorophenyl)ethyl]-2-pyridinyl]-1-methyl-4-piperidinyl methanone hydrochloride To a solution of compound 3-[2-(3-chlorophenyl)ethyl]-2-pyridinecarbonitrile (118 g; 0.49 mol) in 1.2 L of dry THF was added 395 mL (2.48 N; 0.59 mol) of N-methyl-piperidyl magnesium chloride over 0.5 h while the temperature was maintained at 40°–50° C. by cooling with water as necessary. The reaction mixture was maintained at 40°–50° C. for an additional 0.5 h. The reaction was quenched to below pH 2 by the addition of 2N hydrochloric acid and the resulting solution was stirred at 25°–30° C. for 1 h. The bulk of the THF was removed by distillation and the pH of the solution adjusted to 3.5 by the addition of aqueous sodium hydroxide. The mixture was cooled to 5° C. and the product was collected by filtration, washed with cold water and dried under vacuum at 60° C. to give 168 g (91%) of [3-[2-(3-chlorophenyl) ethyl]-2-pyridinyl]-1-methyl-4-piperidinyl methanone hydrochloride as a crystalline solid: mp 183°-185° C.; NMR (200 MHz, DMSO)δ2.72 (s,3H), 2.8-2.9 (m,2H) 3.0-3.2 (m,4H), 3.3-3.5 (m,3H), 3.9-4.1 (m,1H), 7.2-7.3 (m,1H), 7.3-7.4 (m,3H), 7.57 (dd,1H,J=6, 4Hz), 7.84 (dd,1H, J=6, 1.2 Hz), 8.59 (dd,1H,J=4, 1.2 Hz), 10.95 (br s, 1H); mass spectrum m/e (rel intensity) 345M+2 (32), 343M+ (100). Anal. Calcd for $C_{20}H_{24}N_2OCl_2$: C,63.32; H,6.38; N,7.39; Cl,18.69. Found: C,63.45; H,6.47; N,7.40; Cl, 18.49.

E.
8-Chloro-6,11-dihydro-11-(1-methyl-4-piperidinylidene)-5H-benzo[5,6]cyclohepta[1,2-b]pyridine To a solution of [3-[2-(3-chlorophenyl)ethyl]-2-pyridinyl]-1-methyl-4-piperidinyl methanone hydrochloride (59.0 g; 0.15 mol) in 120 mL (120 g; 6.0 mol) of hydrofluoric acid at −35° C. was added boron trifluoride (44.3 g; 0.66 mol) over 1 h. The reaction was quenched using ice water and potassium hydroxide to a final pH of 10. The product was extracted into toluene which was washed with water and brine. The toluene solution was concentrated to a residue which was triturated with hot hexanes. Insoluble salts were removed by filtration and the filtrate was concentrated to give as a main product 45.7 g (HPLC purity 96%, yield 91%) of 8-chloro-6,11-dihydro- 11-(1-methyl-4-piperidinylidene)-5H-benzo[5,6]cyclohepta[1,2-b]pyridine as an off-white solid: mp 116°-119° C.; NMR (200 MHz, CDCl₃)δ2.0-2.2 (m,2H), 2.27 (s,3H), 2.3-2.6 (m,4H), 2.6-3.0 (m,4H), 3.3-3.6 (m,2H), 7.0-7.2 (m,4H), 7.44 (dd,1H,J=8, 2 Hz), 8.42 (dd,1H,J=3, 2 Hz); mass spectrum, m/e (rel intensity) 327M+3 (28), 325M+1 (100) Anal. Calcd. for $C_{20}H_{21}N_2Cl$: C,73.94; H,6.52; N,8.63; Cl,10.92. Found: C,73.88; H,6.48; N,8.69; Cl10.80. This material was found to include the two corresponding fluoro-substituted compound of the invention as discussed further below.

F.
8-Chloro-6,11-dihydro-11-(1-ethoxycarbonyl-4-piperidylidene)-5H-benzo[5,6]cyclohepta[1,2-b]pyridine Ethyl chloroformate (40.4 mL; 45.9 g; 0.423 mol) was added slowly to a hot (-80° C) toluene solution (320 mL) of the 8-chloro-6,11-dihydro-11-(1-methyl-4-piperidinylidene)-5H-benzo[5,6]cyclohepta[1,2-b]pyridine (45.7 g; 0.141 mol) from Example 1E containing the two corresponding fluoro-substituted compounds of the invention. Following complete addition, the temperature was maintained at 80° C. for 1 h. The reaction mixture was cooled to ambient temperature and the toluene solution washed with water which was adjusted to pH 10 with aqueous sodium hydroxide. The organic layer was concentrated to a residue which was dissolved in hot acetonitrile and decolorized with charcoal. The solution was concentrated to a crystalline slurry which was cooled (5° C). 8-chloro-6,11-dihydro-11-(1-ethoxycarbonyl-4-piperidylidene)-5H-benzo[5,6-]cyclohepta [1,2-b]pyridine containing the two corresponding fluoro-substituted compounds of the invention as discussed in Examples 1G below was isolated by filtration yielding 42.4 g: m.p. 134.5°-136° C.; NMR (400 MHz, CDCl₃)δ1.25 (t,3H,J=8 Hz), 2.3-2.4 (m,3H), 2.4-2.5 (m,1H), 2.7-2.9 (m,2H), 3.1-3.2 (m,2H), 3.3-3.4 (m,2H), 3.81 (br s, 2H), 4.13 (q,2H,J=8 Hz), 7.1-7.3 (m,4H), 7.43 (dd,1H,J=9,2 Hz), 8.40 (d,1H,J=5 Hz); mass spectrum, m/e (relative intensity) 385M+3 (35), 383 M+1 (100). Anal. Calcd. for $C_{22}H_{23}N_2ClO_2$: C,69.00; H,6.05; N,7.32; Cl9.26. Found: C,69.37; H,6.09; N,7.35; Cl 9.37.

G. Isolation of Ethyl 4-[8-chloro-6,11-dihydro-5H-benzo[5,6]cyclohepta[1,2-b]pyridin-11-yl]-4-fluoro-1-piperidenecarboxylate and ethyl 4-[8-chloro-11-fluoro-6,11-dihydro-5H-benzo[5,6]cyclohepta[1,2-b]pyridin-11-yl]-1-piperidenecarboxylate The mother liquor from Example 1F (9.8 g) was dissolved in methanol and chromatographed on 2 C-18 cartridges on a Waters Prep 500 eluted with 3:7 (pH 7.8 phosphate buffer:MeOH). Appropriate fractions were combined and concentrated to an aqueous solution. The products were extracted into methylene chloride which was dried (MgSO₄) and concentrated to a residue. This resulted in 1.0 g of ethyl 4-[8-chloro-6,11-dihydro-5H-benzo[5,6]cyclohepta[1,2-b]pyridin-11-yl]-4-fluoro-1-piperidenecarboxylate (Compound A) and 2.5 of ethyl 4-[8-chloro-11-fluoro-6,11-dihydro-5H-benzo[5,6]cyclohepta[1,2-b]pyridin-11-yl]-1-piperidinecarboxylate (Compound B). These compounds had the characteristics as described in Example 2 and 3.

EXAMPLE 2

Characterization of Ethyl 4-[8-chloro-6,11-dihydro-5H-benzo[5,6]cyclohepta[1,2-b]pyridin-11-yl]-4-fluoro-1-piperidenecarboxylate m.p. 149°-153° C.; NMR (200 MHz, CDCl₃)δ1.24 (t,3H,J=6 Hz); 1.6-1.9 (m,4H); 2.7-3.2 (m,4H); 3.4-4.1 (m,4H); 4.14 (q,2H,J=6 Hz); 4.35 (d,1H,J=32 Hz); 7.0-7.2 (m,4H); 7.48 (dd,1H,J=8,1 Hz); 8.34 (dd,1H,J=4, 1Hz); mass spectrum, m/e (rel intensity) 403M+1 (34) Anal. Calcd. for $C_{22}H_{24}N_2O_2ClF$: C,65.91; H,5.90; N,6.70; Cl8.94. Found: C,66.00; H,5.91; N,6.78; Cl 8.94.

EXAMPLE 3

Characterization of Ethyl 4-[8-chloro-11-fluoro-6,11-dihydro-5H-benzo[5,6]cyclohepta[1,2-b]pyridin-11-yl]-1-piperidinecarboxylate m.p. 62-73° C.; NMR (400 MHz, CDCl₃)δ1.22 (t,3H,J=7 Hz); 1.2-1.3 (m,1H); 1.4-1.5 (m,1H); 1.5-1.7 (m,1H); 1.68 (s,2H); 2.5-2.7 (br s, 2H); 2.8-3.1 (m,2H); 3.3-3.5 (m,2H); 4.08 (q,3H,J=7 Hz); 4.1-4.2 (m,1H); 7.1-7.2 (m,2H); 7.25 (s,1H); 7.45 (d,1H,J=6 Hz); 7.63 (d,1H,J=6 Hz); 8.55 (s,1H). Mass spectrum, m/e (rel intensity) 403M+1 (72) Anal. Calcd for f$C_{22}H_{24}N_2O_2ClF$: C,65.91; H,5.90; N,6.70; Cl8.94. Found: C,65.58; H,6.00; N,6.95; Cl8.80.

The following examples illustrate the preparation of tablets and capsules using as the active compound any of the compounds of formula I, e.g., Compound A or B above.

Example 4

Pharmaceutical Dosage Form Examples

Example A

| No. | Ingredient | mg/tablet | mg/tablet |
|---|---|---|---|
| 1. | Active Compound | 100 | 500 |
| 2. | Lactose USP | 122 | 133 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix items nos. 1 and 2 in a suitable mixer for 10–15 minutes. Granulate the mixture with item no. 3. Mill the damp granules through a coarse screen (e.g., ¼″) if needed. Dry the damp granules. Screen the dried granules if needed and mix with item no. 4 and mix for 10–15 minutes. Add item no. 5 and mix for 1–3 minutes. Compress the mixture to appropriate size and weight on a suitable tablet machine.

Example B

| | Capsules | |
|---|---|---|
| No. | Ingredient | mg/capsule | mg/capsule |
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
|  | Total | 250 | 700 |

Method of Manufacture Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

While the present invention has been described in connection with certain specific embodiments thereof, it will evident to one of ordinary skill in the art that many alternatives, modifications and variations may be made. All such alternatives, modifications and variations are intended to be included within the spirit and scope of the invention.

We claim:

1. A compound represented by structural formula I

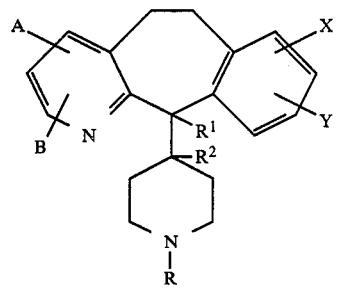

or a pharmaceutically acceptable salt thereof, wherein:

A, B, X and Y may be the same or different, and each independently represents H, halo, $-CF_3$, $-OR^{10}$, $-C(O)R^{10}$, $-SR^{10}$, $-N(R^{10})_2$, $-OC(O)R^{10}$, $-CO_2R^{10}$, $-OCO_2R^{11}$, alkyl, alkenyl or alkynyl, alkyl, alkenyl or alkynyl, which alkyl or alkenyl groups may be substituted with halo, $-OR^{10}$, or $-CO_2R^{10}$;

$R^{10}$ represents H, alkyl or aryl;

$R^{11}$ represents alkyl or aryl;

$R^1$ and $R^2$ may be H and F respectively or F and H respectively; and

R is H, alkyl or $-CO_2R^{10}$ wherein $R^{10}$ is as previously defined.

2. A compound of claim 1 wherein A, B, X and Y may be the same or different and each independently represents H or halo.

3. A compound of claim 2 wherein one of A, B, X and Y is halo and the others are H.

4. The compound of claim 3 wherein one of X or Y is halo and A, B and the other of X or Y are H.

5. The compounds of claim 4 wherein the halo X or Y is chlorine.

6. A compound according to claim 4 wherein R is $CO_2R^{10}$.

7. The compounds of claim 6 wherein $R^{10}$ is selected from H or alkyl.

8. The compounds of claim 7 wherein $R^{10}$ is alkyl.

9. The compounds of claim 8 wherein $R^{10}$ is ethyl.

10. The compounds of claim 9 wherein $R^1$ is fluorine and $R^2$ is H.

11. A compound of claim 1 having the name:.
ethyl 4-[8-chloro-6,11-dihydro-5H-benzo[5,6]cyclohepta[1,2-b]pyridin-11-yl]-4-fluoro-1-piperidine carboxylate; or
ethyl 4-[8-chloro-11-fluoro-6,11-dihydro-5H-benzo[5,6-]cyclohepta[1,2-b]pyridin-11-yl]-1-piperidine carboxylate.

12. A compound of claim 10 having the formula:

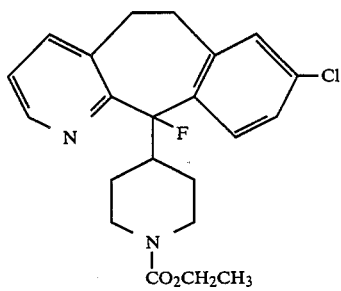

13. A pharmaceutical composition which comprises a compound having structural formula I as defined in claim 1, in combination with a pharmaceutically acceptable carrier.

14. A method for treating allergic reactions in a mammal comprising administering to said mammal an antihistaminic effective amount of a compound as claimed in claim 1.

* * * * *